United States Patent [19]

*Joly et al.

[11] Patent Number: 5,811,626
[45] Date of Patent: Sep. 22, 1998

[54] PARAFFIN ALKYLATION PROCESS

[75] Inventors: Jean-François Joly, Lyons; Alain Forestiere, Vernaison; Jean-Luc Duplan, Irigny; Eric Benazzi, Montesson, all of France

[73] Assignee: Institut Francais du Petrole, France

[ * ] Notice: The term of this patent shall not extend beyond the expiration date of Pat. No. 5,712,213.

[21] Appl. No.: 620,454

[22] Filed: Mar. 22, 1996

[30] Foreign Application Priority Data

Mar. 24, 1995 [FR] France .................................. 95 03591

[51] Int. Cl.$^6$ ...................................................... C07C 2/62
[52] U.S. Cl. ........................................... 585/731; 585/720
[58] Field of Search ..................................... 585/709, 721, 585/714, 731, 720, 704, 710

[56] References Cited

U.S. PATENT DOCUMENTS

| | | | |
|---|---|---|---|
| 2,433,944 | 1/1948 | Draeger et al. ...................... | 260/683.4 |
| 4,214,115 | 7/1980 | Makovec et al. ........................ | 585/716 |
| 5,444,175 | 8/1995 | Joly et al. ................................ | 585/714 |
| 5,491,278 | 2/1996 | Angstadt et al. ....................... | 585/731 |

FOREIGN PATENT DOCUMENTS 0 584 006   2/1994   European Pat. Off. .

*Primary Examiner*—Glenn Caldarola
*Assistant Examiner*—Thuan D. Dang
*Attorney, Agent, or Firm*—Millen, White, Zelano & Branigan, P.C.

[57] ABSTRACT

Disclosed is a process for the alkylation of an isoparaffin by an olefin in the presence of a catalyst. In the process, a portion of the isoparaffin recovered after extraction from the reaction zone (R) is recycled to the reaction zone and the feed is periodcally injected into the reaction zone while the recycled isoparafin fraction is continuously injected into the reaction zone.

22 Claims, 1 Drawing Sheet

PARAFFIN ALKYLATION PROCESS

BACKGROUND OF THE INVENTION

The present invention concerns a novel process for the alkylation of at least one isoparaffin, preferably isobutane, by at least one olefin generally containing 3 to 6 carbon atoms per molecule.

Spark ignition internal combustion engines, in particular high compression ratio engines, require fuels with high octane numbers, i.e., mainly constituted by highly branched paraffinic hydrocarbons. The alkylation of isoparaffins (isobutane and/or isopentane) by olefins which preferably contain 3 to 6 carbon atoms per molecule can produce such products. The reaction requires the use of highly acidic catalysts, mainly to reduce side reactions, such as hydride extraction from the olefin and polymerization which produce less highly branched hydrocarbons with low octane numbers and unsaturated hydrocarbons, cracking reactions and dismutation reactions.

Existing processes for the production of hydrocarbons by alkylation of an isoparaffin by olefins use either sulphuric acid or hydrofluoric acid as the catalyst. In those processes, the acidic catalyst constitutes a liquid phase which is brought into contact with the liquid isoparaffin-olefin mixture to form an emulsion. Those processes are expensive and encounter major problems regarding safety of personnel and the environment. In order to overcome these problems, catalytic systems other that sulphuric acid and hydrofluoric acid in the liquid phase have been sought.

A number of patents claim the use of heterogeneous catalysts (alumina combined with $BF_3$, for example) in Grignard type stirred reactors (International Patent WO 92/03395, United States patents U.S. Pat. No. 4,918,255, U.S. Pat. No. 3,655,813). That use of the catalyst has a number of drawbacks, namely the destruction of the catalyst by attrition over time. Further, obtaining short residence times for hydrocarbons in the reactor is difficult to achieve.

The use of fixed bed(s) of heterogeneous alkylation catalysts has been described in European patent application EP-A-0 433 954, and in United States patents U.S. Pat. No. 3,852,371 and U.S. Pat. No. 3,976,713; in that case, obtaining very high dilution of the olefin close to the catalyst grains is difficult and further, large pressure drops are associated with the use of catalysts with small granulometry.

In the prior art, the feed to be treated is always introduced under continuous conditions. No document in the prior art refers to transient conditions for introducing the feed in the case of the alkylation of at least one isoparaffin by at least one olefin.

SUMMARY OF THE INVENTION

The present invention concerns a process for the catalytic alkylation of at least one isoparaffin, for example isobutane and/or isopentane, by at least one olefin, in the presence of at least one solid or liquid catalyst, to produce at least one product, for example belonging to the group constituted by dimethylbutanes, trimethylpentanes, trimethylhexanes and trimethylheptanes.

The process of the present invention improves the service life of catalysts for alkylation of isoparaffins by olefins.

In particular, it is characterized in that the olefin in the feed is periodically injected or, preferably, the olefin in the feed is injected under conditions which in this document will arbitrarily be termed "transient conditions" for introduction of the feed to be treated into the reactor. The term "feed to be treated" means a mixture of hydrocarbons containing at least one isoparaffin, for example isobutane and/or isopentane, and at least one olefin preferably containing 3 to 6 carbon atoms per molecule in proportions which generally and preferably correspond to the stoichiometry of the alkylation reaction. The term "transient conditions" means discontinuous or periodic injection of the feed over time. The process of the present invention, as will be shown below, preferably employs recycling of at least a fraction of at least one isoparaffin termed the recycling isoparaffin. The recycled isoparaffin is preferably and generally continuously introduced into the reactor rather than employing "transient conditions".

When the olefin is brought into contact with the catalyst, as may be envisaged in the present invention, it generally forms a complex with the catalyst, whether the catalyst is solid or liquid. Thus a complex-isoparaffin suspension is present, for example, in the alkylation zone when the catalyst is solid.

The complex formed between the olefin and the catalyst results from a reaction which involves at least one proton $H^+$, initially present in the catalyst or originating from one of the compounds present. Without subscribing to a particular theory, the interaction between the olefin and the proton $H^+$ leads to the formation of a carbocation $R^+$. The counter-ion $X^-$ associated with the carbocation is a species belonging to the catalyst. As an example, when the catalyst comprises the acid phase $H_2SO_4$, $X^-$ is $HSO_4^-$; HF: $X^-$ is $F^-$; $CF_3SO_3H$: $X^-$ is $CF_3SO_3^-$; $SbF_5$,HF: $X^-$ is $SbF_6^-$. When the catalyst is sulphuric acid and when the olefin is but-1-ene, the complex is the compound $nC_4^+SO_4H^-$.

Without subscribing to a particular theory, the transient operating conditions for the olefin in the feed, one of the characteristics of the process of the invention, can in this particular case improve control of the complex formed between the olefin and the catalyst, in particular by preventing accumulation of the complex. The cycle time (period of time between two successive injections of feed) is selected so that complex conversion is complete.

More generally, it has been shown that the use of transient conditions with one of the reactants can considerably improve the service life of the catalyst. This improvement is valid for a number of solid or liquid alkylation catalysts, in particular solid catalysts, and is independent of the type of reactor used (fixed bed, entrained or circulating bed, expanded bed, fluidized bed, Grignard type reactor . . . ).

Alkylation of an isoparaffin by olefins is characterized by high exothermicity (about 20 kcal/M of butene transformed, i.e., 83.6 kJ/M of butene transformed). The reaction zone in the process of the present invention enables alkylation to be carried out under the best conditions for alkylation of isoparaffin(s) by at least one olefin, and in particular to obtain good homogeneity of temperature and of reactant concentration.

In the isoparaffin alkylation process of the present invention, the operating conditions in reaction zone R, and more particularly the temperature and pressure, are selected so that the mixture, constituted by the isoparaffin and the reaction products, is liquid. Further, it is important that the catalyst, especially if it is solid, is immersed in the liquid to ensure good overall liquid-solid contact. This avoids the occurrence of dry zones in the reactor, which zones may be responsible for lack of thermal stability, since the dry zones can reach high temperatures due to the fact that the reaction can completely occur in the gaseous phase in these regions.

Various techniques have been proposed using a continuous liquid phase, and when the catalyst is solid it can be used as a suspension (expanded bed or stirred bed), as an ebullating bed or as a fixed bed.

The process of the present invention is particularly suitable for heterogeneous alkylation catalysts.

In the process of the present invention, the catalyst present in zone R is preferably selected from solid catalysts which are known to the skilled person, more preferably from the following catalysts:

- a catalyst comprising at least sulphuric acid impregnated into an organic or inorganic porous support, such as the catalysts described in European patent applications EP-A-0 559 511, EP-A-0 539 277, EP-A-0 542 612, EP-A-0 542 620, EP-A-0 643 992, EP-A-0 643 993, EP-A-0 645 183 and EP-A-0 645 184;
- a catalyst comprising a mixture containing at least one halide of a compound selected from the group formed by aluminum and boron, and at least one quaternary ammonium halide and/or amine halohydrate, such as the catalyst described in European patent application EP-A-0 553 009.

One of the preferred solid catalysts used in the present invention preferably comprises silica and sulphuric acid, the silica being completely impregnated with sulphuric acid. The silica is generally selected so that its total pore volume is greater than 0.5 cm$^3$/g. The catalyst obtained after impregnation is generally such that the sulphuric acid content is greater than 45% by weight, preferably greater than 75%. The silica can contain impurities such as oxides, alkalis, alkaline-earths, aluminum compounds or any other impurity which is known to the skilled person, the total quantity of impurities not exceeding 2% by weight with respect to the silica. The sulphuric acid concentration is advantageously in the range 90% to 100% by weight, preferably in the range 97% to 100% by weight and more preferably in the range 98% to 100% by weight. Before impregnation, additives aimed at improving catalytic performance can be added to the $H_2SO_4$ acidic phase. Examples of such additives are the trifluoromethanesulphonic acid $CF_3SO_3H$ and acid $HB(SO_4H)_4$, and preferably boric acid $BO_3H_3$ or boric anhydride. Preferred catalysts (sulphuric acid on silica type, preferably doped with a boron compound) produce results which are superior to those which would be obtained with more conventional silica type catalysts doped with $SbF_3$ or $SbF_5$.

The average diameter of the preferred solid catalyst particles, mainly constituted by substantially spherical grains, is generally in the range 0.1 to 200 m, preferably in the range 10 to 80 m, and more preferably in the range 10 to 60 m.

The invention concerns a process for the alkylation of at least one isoparaffin by at least one olefin in the presence of a catalyst, the process being characterized in that the olefin is introduced periodically into the reaction zone.

The invention also concerns a process for the alkylation of at least one isoparaffin by at least one olefin in the presence of a catalyst, the process being characterized in that the feed comprising the isoparaffin and the olefin, preferably in a stoichiometric mixture, is introduced periodically into a reaction zone.

The invention particularly concerns a process for the alkylation of at least one isoparaffin by at least one olefin in the presence of an alkylation catalyst, consisting of treating a feed (i) comprising a mixture, preferably substantially stoichiometric, of at least one isoparaffin and at least one olefin, the process being characterized in that at least a portion of the isoparaffin fraction recovered after extraction from the reaction zone is recycled to the reaction zone and in that the feed is injected periodically into the reaction zone and the isoparaffin fraction recycled to the reaction zone is injected continuously into said reaction zone.

The process of the present invention is an alkylation process in which a feed comprising at least one isoparaffin, preferably at least one element selected from the group formed by isobutane and isoparaffin, more preferably isobutane, and at least one olefin, generally containing 3 to 6 carbon atoms per molecule, is treated in the presence of a liquid or solid catalyst; said process comprising:

a) introducing the following compounds into, and bringing them into contact with the catalyst present in, at least one reaction zone R:
  (i) said feed, preferably introduced at least to the inlet to a zone R;
  (ii) the liquid effluent described at b), introduced at least to the inlet to zone R, preferably introduced in its entirety to the inlet to zone R; and
  (iii) the liquid effluent described at d), preferably introduced at least to the inlet to zone R, b) recycling a portion of the liquid effluent leaving reaction zone R to the inlet to said zone R;

c) introducing a further portion of the liquid effluent leaving reaction zone R to an isoparaffin/normal-paraffin/alkylate separation zone S;

d) recycling at least the major portion of the isoparaffin-rich effluent from zone S to reaction zone R;

e) obtaining an alkylate as a product, extracted from the lower part of zone S; and optionally f) obtaining normal-paraffin as a purge from zone S;

said process being characterized in that compound
(i) is injected periodically into zone R and in that compound (iii) is injected continuously into zone R.

In a preferred implementation, the feed, i.e., compound (i) described at a), is introduced at a plurality of points in zone R. These different injection points for compound (i) are distributed along the reaction zone, and one of the injection points is the inlet to said zone. The distribution is such that it is the most advantageous for the evolution of the reaction, depending on the operating conditions and the compounds present in zone R.

In a further preferred implementation, compound (ii) described at a), is introduced at a plurality of points in zone R. These different injection points for compound (ii) are distributed along the reaction zone, and one of the injection points is the inlet to said zone. The distribution is such that it is the most advantageous for the evolution of the reaction, depending on the operating conditions and the compounds present in zone R.

In a still further preferred implementation, compound (iii) described at a), is introduced at a plurality of points in zone R. These different injection points for compound (iii) are distributed along the reaction zone, and one of the injection points is the inlet to said zone. The distribution is such that it is the most advantageous for the evolution of the reaction, depending on the operating conditions and the compounds present in zone R.

Preferably, the fractions of compounds (i) to (iii) described at a) which are introduced together into zone R are mixed together either in part or completely, preferably completely, before being introduced into said zone.

The temperature in the zone R is generally in the range −30° C. to +5° C., preferably in the range −15° C. to +5° C., and the pressure is such that all the product injected into zone R, at whatever the level of injection, is liquid on injection into said zone.

Preferably, the feed is dried over a molecular sieve and selectively hydrogenated before its introduction into zone R.

The ratio of the mass flow rate of the recycled portion of liquid effluent leaving reaction zone R described in b) and the mass ratio of compound (iii) is generally in the range 2 to 10000, preferably in the range 5 to 1000.

In one implementation, the feed to be treated is introduced under transient conditions which comprise two periods of time: 1) a period during which the feed and the recycled isoparaffin fraction are introduced into reaction zone R, and 2) a period during which only said recycled isoparaffin fraction is introduced into zone R. Period 1), during which the feed is injected, is preferably in the range 0.1 to 10 seconds long, and period 2), during which the feed is not injected, is preferably in the range 30 seconds to 10 minutes long. To compensate for catalyst deactivation, period 2) can be increased in duration without changing that of period 1).

The mass flow rate of the feed introduced into reaction zone R during the first period is generally such that the ratio between the number of moles of acid in the catalyst and the number of moles of olefin injected during said period is in the range 10 to 1000, preferably in the range 20 to 800 and more preferably in the range 50 to 400.

The reactants are generally introduced so that the hourly space velocity, expressed as the weight of olefin(s) introduced per unit weight of catalyst present in zone R per hour, is generally in the range 0.01 to 10 $h^{-1}$, preferably in the range 0.02 to 2 $h^{-1}$, and more preferably in the range 0.025 to 1 $h^{-1}$.

Generally, the molar ratio [sum of isoparaffin present in compounds (i) and (iii) described at a)]/[sum of the olefin(s) present in compounds (i) and (ii) described at a) and b)] is in the range 1 to 100, preferably in the range 3 to 50, and more preferably in the range 5 to 25.

One or more reactors can be used in the process of the present invention. When a plurality of reactors in series is used, it is advantageous to introduce the isoparaffin originating from separation zone S (compound (iii)) to the inlet to the first reactor, the olefins then being introduced to the inlet to each reactor.

When using reactors in parallel, each reactor will receive a portion of (recycled) effluent (iii) and appropriate quantities of olefins (for example butenes) and isoparaffin (for example isobutane) (fresh and recycled from the head of separation zone S) via distribution means which are known to the skilled person.

In a preferred implementation of the invention, catalyst is extracted continuously or discontinuously from reaction zone R and fresh catalyst is introduced continuously or discontinuously to maintain constant the quality of the alkylate produced.

BRIEF DESCRIPTION OF THE DRAWING

The accompanying

The liquid mixture comprising at least one isoparaffin, preferably at least one element selected from the group formed by isobutane and isoparaffin, and at least one olefin generally containing 3 to 6 carbon atoms per molecule, is introduced into a reaction zone R via line 1 then via line 2 after mixing with the liquid effluents from lines 3 then 4. The inlets for the catalyst are not shown.

A heat exchanger E located in line 4 eliminates the heat released by the reaction and maintains the temperature of the liquid in the reactor at the desired value.

A portion of liquid effluent leaving zone R via line 5 is recycled to reaction zone R via line 4 then via line 2 after mixing with the liquid effluents from lines 1 and 3. The major portion of the other portion of liquid effluent leaving reaction zone R, which is not recycled to the inlet to zone R, is sent via line 6 to an isoparaffin/normal-paraffin/alkylate separation zone.

The alkylate separated in zone S is extracted from the unit as a product via line 7. Normal-paraffin is extracted as a side stream from zone S, as a purge via line 8. The isoparaffin-rich liquid fraction extracted overhead from zone S is recycled to the inlet to reaction zone R via line 3.

Figure 1:
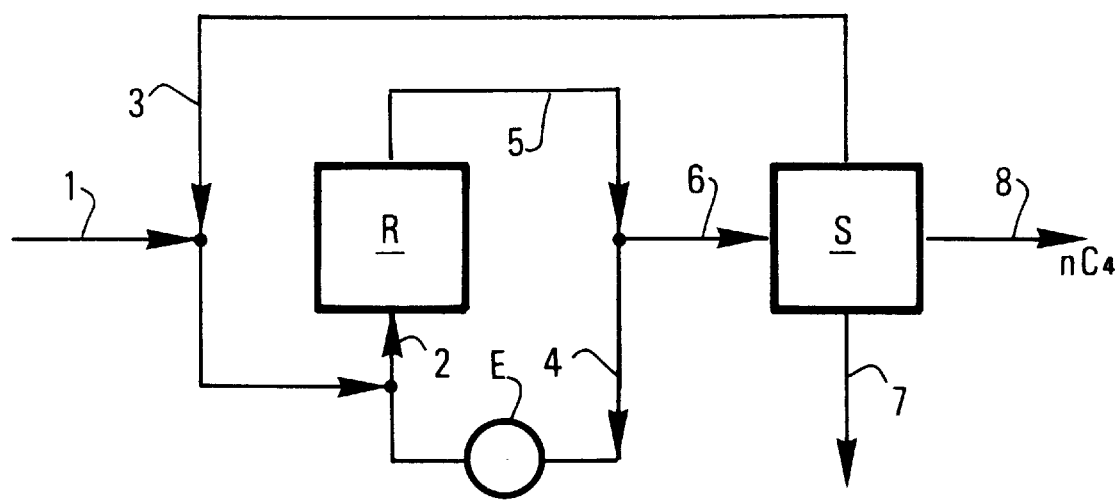
FIG. 1 illustrates the invention, more precisely a preferred implementation of the process of the present invention, without in any way limiting its scope.
Figure 2:
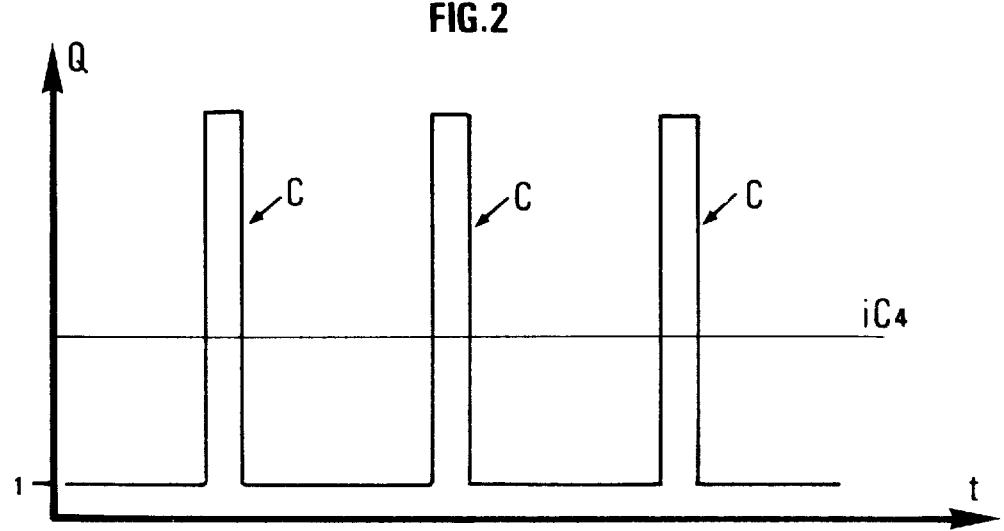

FIG. 2 shows the evolution with time of the mass flow rates Q of isoparaffin (iC4) recycled from the head of separation zone S, line 3, and of feed C, line 1.

EXAMPLES

Catalyst composition 15 grams of silica with a total pore volume of 2.6 $cm^3/g$, a specific surface area of 420 $m^2/g$ and average particle diameter of 75 m were activated by heating in a stream of dry $N_2$ at 500° C. for 12 hours. The activated silica was stored under dry nitrogen. 2.97 g of boric acid was then added to 100 g of a solution of sulphuric anhydride in sulphuric acid containing 11.5% by weight of sulphuric anhydride and 88.5% by weight of sulphuric acid, to obtain 102.97 g of acidic phase. Following reaction of the sulphuric anhydride and the boric acid in the presence of sulphuric acid in respective molar ratios of 3/1/1, an acid phase was obtained which contained the compound $HB(HSO_4)_4$ in solution in $H_2SO_4$ and comprising 18.6% by weight of $HB(HSO_4)_4$ and 81.4% by weight of $H_2SO_4$.

10 g of activated silica was then dry impregnated with 47.5 g of the phase described above. The solid obtained had a weight content of acid phase ($H_2SO_4+HB(HSO_4)_4$) of 82.6% by weight and 67.23% by weight of sulphuric acid. The number of moles of sulphuric acid per gram of catalyst was thus $6.86 \times 10^{-3}$ mol.

The catalyst was stored under argon, protected from moisture.

Conditions for alkylation of isoparaffin by but-2-ene

Alkylation was carried out in a Grignard type reactor with a volume of 500 $cm^3$, stirred using a propeller turning at 600 revs/min. A portion of the effluent leaving the reactor was recycled to the reactor. The recycle flow rate was 600 $cm^3/h$. The portion of effluent which was not recycled to the reactor was sent to an isoparaffin-alkylate separation zone which operated as a flash drum. Analysis of the composition by weight of the alkylate was carried out on the whole of the liquid phase before depressurizing in the flash drum. The alkylation test was carried out at a temperature of −5° C. and a pressure of $5 \times 10^5$ Pa. The mass of catalyst present in the reactor was 25 g.

Two stability tests were carried out on the catalyst using the same average isobutane/butene molar ratio of 40 (dilution of the stoichiometric isobutane+butene feed by recycled isobutane from an isobutane/alkylate separation zone, absent here but simulated by introducing a large excess of isobutane to the reactor inlet). The test of the invention was effected by injecting the olefin under transient conditions, the comparative test being effected using a continuous flow of a mixture of isobutane and butene of the same average composition as that of the preceding test. In both cases the average hourly flow rates for butene were identical and corresponded to a WHSV of 0.1 g of butene/g of catalyst/h.

In Examples 1 and 2, the excess isobutane was not recycled. Examples 1 and 2 used sulphuric acid as the catalyst.

Example 1
not in accordance with the invention

The reactor was continuously supplied with an isobutane—butene mixture containing 2.36% by weight of butene. The hourly flow rate of the mixture was 194 cm$^3$/h.

The productivity of the catalyst, measured by the alkylation test and corresponding to a $C_8$ selectivity of greater than or equal to 80% by weight, was measured as 28 g of alkylate per g of catalyst.

Example 2
in accordance with the invention

The reactor was supplied with a continuous flow of isobutane of 185.3 cm$^3$/h. Every 60 seconds, a stoichiometric mixture of isobutane and butene (containing 49% by weight of butene) was introduced at a flow rate of 258 cm$^3$/h for 2 seconds. The olefin was thus injected for 2 seconds every minute. This cycle was repeated throughout the alkylation test period.

The quantity of butene introduced over the 2 seconds of injection was 0.042 g, i.e., 0.75×10$^{-3}$ mol. The sulphuric acid/butene molar ratio was thus 227.

The productivity of the catalyst, measured by the alkylation test and corresponding to a $C_8$ selectivity of more than or equal to 80% by weight was measured at 110 g of alkylate per g of catalyst.

The use of a transient mode for injecting the olefin substantially improved productivity, and thus the stability, of the catalyst.

We claim:

1. A process comprising alkylating at least one isoparaffin by at least one olefin in the presence of a catalyst comprising silica impregnated with sulfuric acid in a reaction zone, wherein a feed, comprising the isoparaffin and the olefin, is introduced into the reaction zone under transient conditions which comprise two periods of time, a first period during which said feed and a recycled isoparaffin fraction are introduced into the reaction zone and a second period during which only said recycled isoparaffin fraction in introduced into the reaction zone.

2. A process according to claim 1, in which the isoparaffin and olefin are provided in substantially stoichiometric amounts.

3. A process according to claim 1, wherein the first period has a duration in the range of 0.1 to 10 seconds, and the second period has a duration in the range of 30 seconds to 10 minutes.

4. A process according to claim 3, in which the mass flow rate of the feed introduced into reaction zone during the first period is such that the ratio between the number of moles of acid in the catalyst and the number of moles of olefin injected during said period is in the range 10 to 1000.

5. An alkylation process according to claim 1, in which a feed comprising at least one isoparaffin and at least one olefin is treated in the presence of a liquid or solid alkylation catalyst, said process comprising:
   a) introducing the following compounds into, and bringing them into contact with the catalyst present in, at least one reaction zone R:
   (i) said feed,
   (ii) the liquid effluent described at b), introduced at least to the inlet to zone R, and
   (iii) the liquid effluent described at d);
   b) recycling a portion of the liquid effluent leaving reaction zone R to the inlet to said zone R;
   c) introducing a further portion of the liquid effluent leaving reaction zone R to an isoparaffin/normal-paraffin/alkylate separation zone S;
   d) recycling at least the major portion of the isoparaffin-rich effluent from zone S to reaction zone R;
   e) obtaining an alkylate as a product, extracted from the lower part of zone S;
   said process being characterized in that compound (i) is injected periodically into zone R and in that compound (iii) is injected continuously into zone R.

6. A process according to claim 5, in which the feed, i.e., compound (i) described at a), is introduced at a plurality of points in zone R, the different injection points for compound (i) being distributed along the reaction zone, and one of the injection points is the inlet to said zone.

7. A process according to claim 5, in which compound (ii) described at a) is introduced at a plurality of points in zone R, the different injection points for compound (ii) being distributed along the reaction zone, and one of the injection points is the inlet to said zone.

8. A process according to claim 5, in which compound (iii) described at a) is introduced at a plurality of points in zone R, the different injection points for compound (iii) being distributed along the reaction zone, and one of the injection points is the inlet to said zone.

9. A process according to claim 5, in which the fractions of compounds (i) to (iii) described at a) which are introduced together into zone R are mixed together either in part or completely, before being introduced into said zone.

10. A process according to claim 5, in which the ratio of the mass flow rate of the recycled portion of liquid effluent leaving reaction zone R described in b) and the mass ratio of compound (iii) is generally in the range 2 to 10000.

11. A process according to claim 5, in which the reactants are introduced so that the hourly space velocity, expressed as the weight of olefin(s) introduced per unit weight of catalyst present in zone R per hour, is generally in the range 0.01 to 10 h$^{-1}$.

12. A process according to claim 5, in which the molar ratio of the sum of the isoparaffin present in compounds (i) and (iii) described at a) and d) to the sum of the olefin(s) present in compounds (i) and (ii), described at a) and b), is in the range of 1 to 100.

13. A process according to claim 1, in which the temperature in the reaction zone is generally in the range −30° C. to +5° C., and the pressure is such that all the products injected into the reaction zone, whatever the level of injection, is liquid on injection into said zone.

14. A process according to claim 1, in which the feed has been dried over a molecular sieve and selectively hydrogenated before its introduction into the reaction zone.

15. The process of claim 1, wherein at least one isoparaffin is isobutane or isopentane and at least one olefin is an olefin of 3 to 6 carbon atoms.

16. The process of claim 1, wherein the catalyst is a heterogeneous alkylation catalyst.

17. The process of claim 7, wherein the at least one isoparaffin is alkylated with only one olefin.

18. The process of claim 7, wherein the periods wherein the feed is added are separated by periods wherein no olefin feed is added.

19. A process comprising alkylating at least one isoparaffin by at least one olefin in the presence of the catalyst comprising silica impregnated with sulfuric acid in a reaction zone, wherein the at least one olefin is introduced periodically at periods of 0.1 to 10 seconds into a reaction zone.

20. The process of claim 19, wherein the catalyst is a heterogeneous alkylation catalyst.

21. The process of claim 19, wherein the periods wherein the olefin is added are separated by periods wherein no olefin feed is added.

22. The process of claim 19, wherein the time between the periods wherein at least one olefin is introduced are from 30 seconds to 10 minutes.

* * * * *